United States Patent [19]

Nardi et al.

[11] Patent Number: 4,634,712
[45] Date of Patent: Jan. 6, 1987

[54] ANTIHYPERTENSIVE ESTERS OF 1,4-DIHYDRO-2,6-DIMETHYL-3-(ALKOXYCARBONYL OR ALKOXYALKOXYCARBONYL)-4-(SUBSTITUTED PHENYL)-PYRIDINE-5-CARBOXYLIC ACID

[75] Inventors: Dante Nardi; Amedeo Leonardi; Giorgio Bianchi, all of Milan, Italy

[73] Assignee: Recordati S.A., Switzerland

[21] Appl. No.: 734,024

[22] Filed: May 14, 1985

[30] Foreign Application Priority Data

May 24, 1984 [GB] United Kingdom ............... 8413385

[51] Int. Cl.$^4$ .................. C07D 211/90; A61K 31/455
[52] U.S. Cl. ..................................... 514/356; 546/321
[58] Field of Search ......................... 546/321; 514/356

[56] References Cited

U.S. PATENT DOCUMENTS 4,423,052 12/1983 Araki et al. ........................ 546/321

FOREIGN PATENT DOCUMENTS 175165 10/1982 Japan ..................................... 546/321

Primary Examiner—Henry R. Jiles
Assistant Examiner—Dale A. Bjorkman
Attorney, Agent, or Firm—Darby & Darby

[57] ABSTRACT

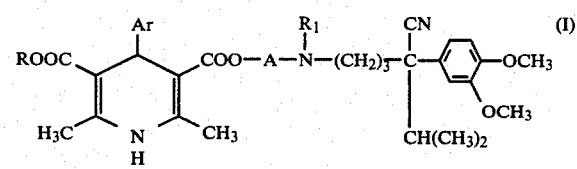

Esters I (Ar=3-nitrophenyl or 2,3-dichlorophenyl, A=$C_2$-$C_6$ alkylene, R=$C_1$-$C_6$ alkyl optionally $C_1$-$C_6$ alkoxy monosubstituted, $R_1$=$C_1$-$C_4$ alkyl) have antihypertensive activity and are effective against coronary heart diseases. They are prepared starting from the aldehyde ArCHO and esters of acetoacetic acid and 3-aminocrotonic acid. Pharmaceutical preparations containing them are also described.

18 Claims, No Drawings

ANTIHYPERTENSIVE ESTERS OF 1,4-DIHYDRO-2,6-DIMETHYL-3-(ALKOXYCARBONYL OR ALKOXYALKOXYCARBONYL)-4-(SUBSTITUTED PHENYL)-PYRIDINE-5-CARBOXYLIC ACID

DESCRIPTION

The invention relates to esters of 1,4-dihydro-2,6-dimethyl-3-(alkoxycarbonyl or alkoxyalkoxycarbonyl)-4-(substituted phenyl)-pyridine-5-carboxylic acid, to their stereochemical isomers and pharmaceutically acceptable salts, to processes for their production and to pharmaceutical compositions containing them.

The invention provides esters of 1,4-dihydro-2,6-dimethyl-3-(alkoxycarbonyl or alkoxyalkoxycarbonyl)-4-(substituted phenyl)-pyridine-5-carboxylic acid, the esters having the general formula I

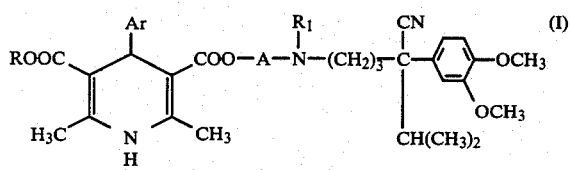

wherein
Ar represents a 3-nitrophenyl or 2,3-dichlorophenyl group,
A represents a straight chain or branched chain alkylene group having from 2 to 6 carbon atoms,
R represents a straight chain or branched chain alkyl group having from 1 to 6 carbon atoms, optionally mono-substituted by an alkoxy group having from 1 to 6 carbon atoms, and
$R_1$ represents an alkyl group having from 1 to 4 carbon atoms,
and further provides pharmaceutically acceptable acid addition salts of such esters.

The invention further provides a process for the preparation of the esters of the general formula I, the process comprising condensing a compound of the general formula II

     Ar—CHO     (II)

wherein Ar is as above defined with a compound of the general formula III

     CH$_3$COCH$_2$COOA$_1$     (III)

wherein A$_1$ represents one of (a) a group R as above defined, (b) a group of the general formula IV

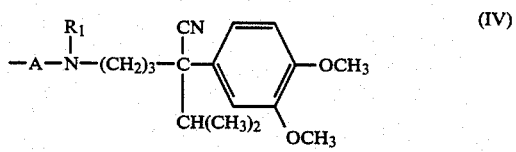

wherein A and $R_1$ are as above defined and (c) a group readily convertible to the group defined in (b) reacting the condensate with a compound of the general formula V

wherein if A$_1$ represents the group defined in (a) then A$_2$ represents either of the groups defined in (b) and (c) and if A$_1$ represents either of the groups defined in (b) and (c) then A$_2$ represents the group defined in (a) to give a compound of the general formula (VI)

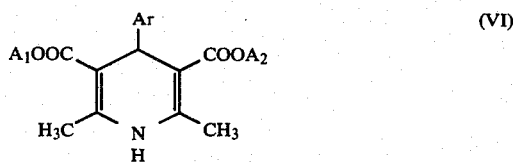

wherein A$_1$, A$_2$ and Ar are as above defined, and if one of the groups A$_1$ and A$_2$ represents a group defined in (c) then converting that one of A$_1$ and A$_2$ to a group defined in (b).

It will be understood that various synthetic routes are encompassed within the above process. The reaction scheme below, wherein X represents a halogen atom and the other variables are as above defined, illustrates some of these.

For example, the esters I may be prepared by condensing a haloalkyl acetoacetate IIIa (III: A$_1$=AX) with an aldehyde II, reacting the condensate with an alkyl or alkoxyalkyl 3-aminocrotonate Va (V: A$_2$=R), and converting the group AX of the resultant pyridine derivative VIa (VI: A$_2$=R, A$_1$=AX) to a group IV by reacting with 4-cyano-4-(3,4-dimethoxyphenyl)-5-methyl-hexylamine or a derivative thereof (VII).

Alternatively the group IV may be introduced into the compound III before ring formation. These routes start from compound IIIb

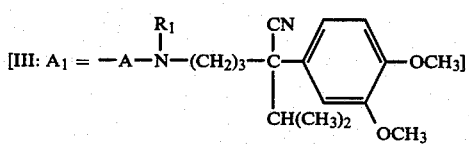

This is available from the amine VII by conventional alkylation to introduce a hydroxyalkyl group HO-A (compound VIII), and the reaction of the alkylated amine with diketene. In one route, compound IIIb is condensed with an aldehyde II and the product is reacted with a 3-aminocrotonate Va.

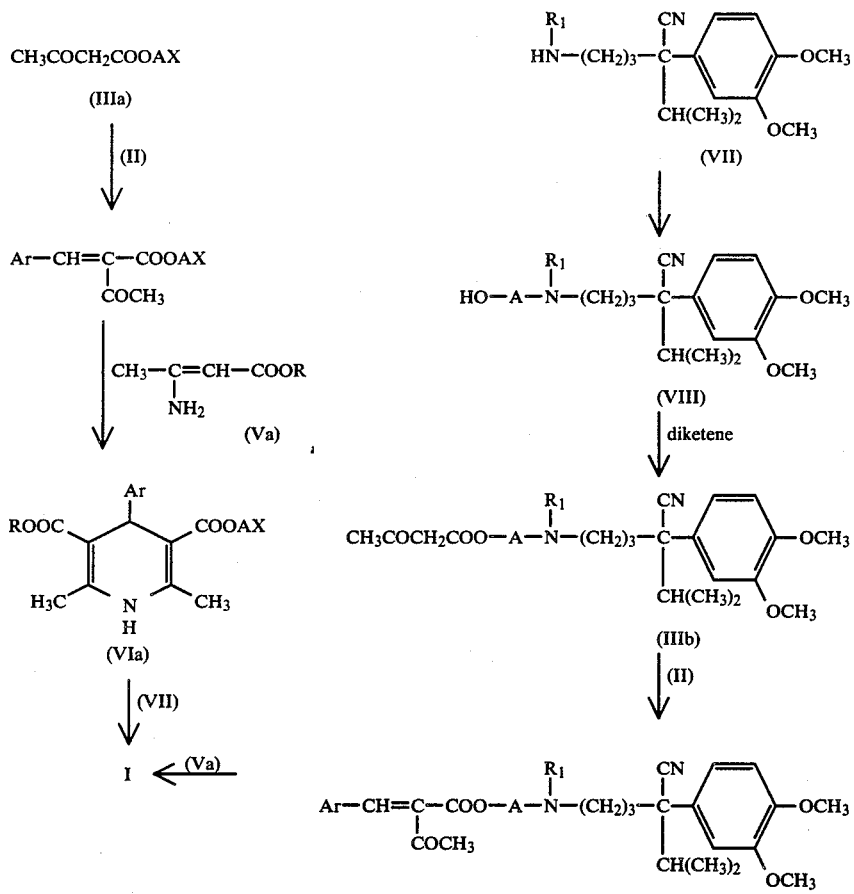

The above process includes a synthesis of the pyridine ring. If a pyridine derivative VIa is already available it is only necessary to condense it with an amine VII. This condensation is itself within the scope of the invention. When X represents a chlorine atom, it is preferably carried out in toluene or xylene under reflux, whereas when X represents a bromine atom it may be carried out in dimethylformamide at lower temperature.

The esters I obtained may be purified according to methods known per se. The pharmaceutically acceptable salts according to the invention may be prepared from the bases in a conventional manner. Preferred pharmaceutically acceptable acid addition salts are those of hydrochloric, sulphuric, maleic, succinic, citric, methanesulphonic and toluenesulphonic acids. Their stereoisomers may be separated in a conventional manner.

The esters I and their salts according to the invention possess a valuable antihypertensive activity and are also effective against coronary heart diseases. Accordingly, the invention also provides a pharmaceutical composition comprising an ester of the general formula I as above defined or a pharmaceutically acceptable salt thereof in admixture with a pharmaceutically acceptable diluent or carrier.

The $LD_{50}$ of the compounds according to the invention was determined in the mouse per os, according to the method described by C. S. Weil (Biometrics, 8, 249, 1952).

The antihypertensive activity of the esters according to the invention was evaluated in male hypertensive rats (SHR, Wister-Kyoto strain, 15–25 weeks old). The determination of blood pressure was performed by an indirect method (M. Gerald et al., Arzneim, Forsch., 18, 1825, 1968). The animals were prewarmed in a heating chamber at a temperature of from 35° to 37° C. for a period of 15 minutes before pressure determination. The compounds tested by oral route were dissolved or suspended in a 0.5% methylcellulose solution. Controls were given only the vehicle. Systolic blood pressure and heart rate were measured 1, 3, 5 and 7 hours after drug administration by means of a tail-cuff and a pulse transducer.

Coronary dilating activity was evaluated in anesthetized normotensive rats (weighing about 500 g), as the ability to antagonize methacholine induced coronary spasm. Rats were instrumented for methacholine infusion into the coronary ostium, while spastic activity was detected as ST segment elevation in $D_2$ ECG recording (K. Sakai et al., J. Pharm. Meth., 5, 325, 1981). The compounds tested by i.v. infusion were dissolved in water:dimethylformamide (9:1 by volume). Activity was detected as normalization of ECG tracing after compounds administration during methacholine infusion.

The results of the tests, given in the Table below, show that the esters are of low toxicity, possess valuable antihypertensive activities and can also be considered effective against coronary hear diseases.

TABLE

| Compound | LD$_{50}$ mg/kg os | ED$_{25}$ SHR os mg/kg | ED$_{50}$ iv mg/kg |
|---|---|---|---|
| 2245 | 278 | 6.8 | 0.301 |
| 2392 | 3000 | 14.9 | — |
| 2404 | 3000 | 17.8 | — |

ED$_{25}$ = antihypertensive activity mg/kg
ED$_{50}$ = coronary dilating activity mg/kg
— = not tested The invention is illustrated by the following Examples.

EXAMPLE 1

Methyl 2-[4-cyano-4-(3,4-dimethoxyphenyl)-5,N-dimethyl-hexylamino]-ethyl 1,4-dihydro-2,6-dimethyl-4-(3-nitrophenyl)-pyridine-3,5-dicarboxylate A solution comprising 3.94 g of methyl 2-chloroethyl 1,4-dihydro-2,6-dimethyl-4-(3-nitrophenyl)-pyridine-3,5-dicarboxylate and 5.78 g of 4-cyano-4-(3,4-dimethoxyphenyl)-5,N-dimethylhexylamine in 12 ml of xylene was refluxed under stirring for 7 hours. At the end of the reaction, the mixture was diluted with ethyl acetate and the solutin wax extracted with dilute hydrochloric acid in order to remove the unreacted amine. The organic solution was dried, the solvent was evaporated off under vacuum, and the residue was washed with diethyl ether, treated with dilute aqueous sodium hydroxide solution and extracted with diethyl ether:ethyl acetate (4:1 by volume). The extract was dried and the solvents were evaporated off under vacuum. The crude product thus obtained was purified by silica gel chromatography, using chloroform as eluent with increasing amounts of ethyl acetate. Pure fractions were collected and evaporated to dryness. The residue was dissolved in methanol, filtered through charcoal, treated with ethanolic hydrogen chloride and evaporated to dryness under vacuum. The residue was washed with warm diethyl ether:acetone mixtures (49:1 and then 24:1 by volume). 2.32 g of the hydrochloride of the title compound (2245) were obtained.
Mp 97°–103° C. (Kofler).

EXAMPLE 2

2-[4-cyano-4-(3,4-dimethoxyphenyl)-5,N-dimethyl-hexylamino]-1-methylethanol

A solution of 18.9 g of 4-cyano-4-(3,4-dimethoxyphenyl)-5,N-dimethyl-hexylamine and 4.5 g of propylene oxide in 40 ml of methanol was allowed to stand for 24 hours at 20° C. A further 0.75 g of propylene oxide was then added, and after 24 hours at 20° C. the solution was refluxed for 1 hour and then evaporated to dryness in vacuo. The oil thus obtained was purified by silica gel chromatography using chloroform as eluent containing increasing amounts of methanol as eluent. The unitary TLC fractions (chloroform:methanol:5N methanolic ammonia 95:5:0.5 by volume) were evaporated to dryness to give 18.78 g of the title compound as an oil.

EXAMPLE 3

2-[4-cyano-4-(3,4-dimethoxyphenyl)-5,N-dimethyl-hexylamino]-1-methylethyl acetoacetate 2.7 ml of diketene was added, over 10 minutes, to a solution of 11.36 g of the compound prepared in Example 2 in 10 ml of toluene at 80° C. When the exothermic reaction was over, the reaction mixture was heated for 2 hours at 80° C. and, after cooling, it was evaporated to dryness in vacuo. The oily residue was then purified by silica gel column chromatography using ehtyl acetate containing decreasing amounts of petroleum ether as eluent. The unitary TLC fractions (chloroform:methanol 95:5 by volume) were evaporated to dryness in vacuo to give 11.61 g of the title compound as an oil.

EXAMPLE 4

2-[4-cyano-4-(3,4-dimethoxyphenyl)-5,N-dimethyl-hexylamino]-1-methylethyl α-acetyl-3-nitrocinnamate hydrochloride A solution of 7.80 g of the compound prepared in Example 3 and 3.26 g of 3-nitrobenzaldehyde in 25 ml of chloroform was saturated with hydrogen chloride at 0° C. After 24 hours at 20° C., the reaction mixture was evaporated to dryness in vacuo and the oil residue was solidified by treatment with diethyl ether. The solid thus obtained was washed with diethyl ether:ethyl acetate 95:5 by volume (6×30 ml) until no trace of 3-nitrobenzaldehyde could be discovered.

8.70 g of the title compound, melting at 75°–100° C., were obtained, as an E-Z isometric mixture, which was used as such for further reactions.

EXAMPLE 5

2-[4-cyano-4-(3,4-dimethoxyphenyl)-5,N-dimethyl-hexylamino]-1-methylethyl α-acetyl-2,3-dichlorocinnamate hydrochloride Operating as described in Example 4, but employing 2,3-dichlorobenzaldehyde instead of 3-nitrobenzaldehyde, the title compound was obtained as a brown oil. The compound was an E-Z isometric mixture and was used as such for further reactions.

EXAMPLE 6

Isopropyl 2-[4-cyano-4-(3,4-dimethoxyphenyl)-5,N-dimethyl-hexylamino]-1-methylethyl 1,4-dihydro-2,6-dimethyl-4-(3-nitrophenyl)-pyridine-3,5-dicarboxylate A solution of 1.38 g of the compound prepared in Example 4 and 0.33 g of ispropyl 3-aminocrotonate in 4 ml of isopropanol was refluxed for 2.5 hours. After cooling, the mixture was evaporated to dryness in vacuo and the residue was dissolved in dichloromethane and washed with an aqueous solution of sodium bicarbonate. The organic phase was dried and evaporated in vacuo to dryness. The residue was purified by flash chromatography on silica gel using petroleum ether containing increasing amounts of acetone as eluent. The unitary TLC fractions (petroleum ether:acetone 7:3 by volume) were evaporated to dryness. The residue was dissolved in diethyl ether and acidified with hydrogen chloride in diethyl ether to give a solid which was collected, washed with diethyl ether and dried. 0.87 g of the hydrochloride hemihydrate of the title compound (2432) melting at 90°–105° C., was obtained.

EXAMPLE 7

Isobutyl 2-[4-cyano-4-(3,4-dimethoxyphenyl)-5,N-dimethyl-hexylamino]-1-methylethyl 1,4-dihydro-2,6-dimethyl-4-(2,3-dichlorophenyl)-pyridine-3,5-dicarboxylate Operating as described in Example 6, but starting from isobutyl 3-aminocrotonate and the compound prepared in Example 5, the hydrochloride hydrate of the title compound (2392), melting at 120°–123.5° C., was obtained.

EXAMPLE 8

2-Propoxy-ethyl 2-[4-cyano-4-(3,4-dimethoxyphenyl)-5,N-dimethyl-hexylamino]-1-methylethyl 1,4-dihydro-2,6-dimethyl-4-(2,3-dichlorophenyl)-pyridine-3,5-dicarboxylate Operating as described in Example 6, but starting from 2-propoxy-ethyl 3-aminocrotonate and the compound prepared in Example 5, the hydrochloride hydrate of the title compound (2404), melting at 102°–105° C., was obtained.

We claim:

1. An ester of 1,4-dihydro-2,6-dimethyl-3-(alkoxycarbonyl or alkoxyalkoxycarbonyl)-4-(substituted phenyl)-pyridine-5-carboxylic acid, the ester having the general formula

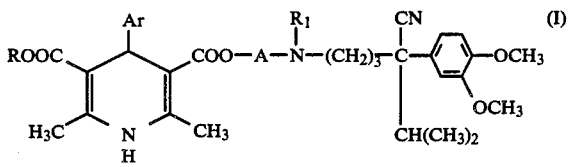

wherein

Ar represents a 3-nitrophenyl or 2,3-dichlorophenyl group,

A represents a straight chain or branched chain alkylene group having from 2 to 6 carbon atoms, R represents a straight chain or branched chain alkyl group having from 1 to 6 carbon atoms, optionally mono-substituted by an alkoxy group having from 1 to 6 carbon atoms, and $R_1$ represents an alkyl group having from 1 to 4 carbon atoms, or a stereoisomer or pharmaceutically acceptable acid addition salt of said ester.

2. Methyl 2-[4-cyano-4(3,4-dimethoxyphenyl)-5,N-dimethyl-hexylamino]-ethyl 1,4-dihydro-2,6-dimethyl-4-(3-nitrophenyl)-pyridine-3,5-dicarboxylate or its hydrochloride.

3. Isopropyl 2-[4-cyano-4-(3,4-dimethoxyphenyl)-5,N-dimethyl-hexylamino]-1-methyl-ethyl 1,4-dihydro-2,6-dimethyl-4-(3-nitrophenyl)-pyridine-3,5-dicarboxylate or its hydrochloride hemihydrate.

4. Isobutyl 2-[4-cyano-4-(3,4-dimethoxyphenyl)-5,N-dimethyl-hexylamino]-1-methylethyl 1,4-dihydro-2,6-dimethyl-4-(2,3-dichlorophenyl)-pyridine-3,5-dicarboxylate or its hydrochloride hydrate.

5. 2-Propoxy-ethyl 2-[4-cyano-4-(3,4-dimethoxyphenyl)-5,N-dimethyl-hexylamino]-1-methylethyl 1,4-dihydro-2,6-dimethyl-4-(2,3-dichlorophenyl)-pyridine-3,5-dicarboxylate or its hydrochloride hydrate.

6. A pharmaceutical composition comprising an effective amount of an ester according to claim 1 or 2 for combatting hypertension in admixture with a pharmaceutically acceptable diluent or carrier.

7. A pharmaceutical composition comprising an effective amount of an ester according to claim 3 or 4 for combatting hypertension in admixture with a pharmaceutically acceptable diluent or carrier.

8. A pharmaceutical composition comprising an effective amount of an ester according to claim 5 for combatting hypertension in admixture with a pharmaceutically acceptable diluent or carrier.

9. A pharmaceutical composition comprising an effective amount of a pharmaceutically acceptable acid addition salt of an ester according to claim 1 or 2 for combatting hypertension in admixture with a pharmaceutically acceptable carrier or diluent.

10. A pharmaceutical composition comprising an effective amount of a pharmaceutically acceptable acid addition salt of an ester according to claim 3 or 4 for combatting hypertension in admixture with a pharmaceutically acceptable carrier or diluent.

11. A pharmaceutical composition comprising an effective amount of a pharmaceutically acceptable acid addition salt of an ester according to claim 5 for combatting hypertension in admixture with a pharmaceutically acceptable carrier or diluent.

12. A pharmaceutical composition comprising an effective amount of an ester according to claim 1 or 2 for combatting coronary heart disease in admixture with a pharmaceutically acceptable diluent or carrier.

13. A pharmaceutical composition comprising an effective amount of an ester according to claim 3 or 4 for combatting coronary heart disease in admixture with a pharmaceutically acceptable diluent or carrier.

14. A pharmaceutical composition comprising an effective amount of an ester according to claim 5 for combatting coronary heart disease in admixture with a pharmaceutically acceptable diluent or carrier.

15. A pharmaceutical composition comprising an effective amount of a pharmaceutically acceptable acid addition salt of an ester according to claim 1 or 2 for combatting coronary heart disease in admixture with a pharmaceutically acceptable carrier or diluent.

16. A pharmaceutical composition comprising an effective amount of a pharmaceutically acceptable acid addition salt of an ester according to claim 3 or 4 for combatting coronary heart disease in admixture with a pharmaceutically acceptable carrier or diluent.

17. A pharmaceutical composition comprising an effective amount of a pharmaceutically acceptable acid addition salt of an ester according to claim 5 for combatting coronary heart disease in admixture with a pharmaceutically acceptable carrier or diluent.

18. A method of controlling hypertension in a mammal afflicted with hypertension which comprises administering to said mammal an effective amount for controlling hypertension of an ester of 1,4-dihydro-2,6-dimethyl-3-(alkoxycarbonyl or alkoxyalkoxycarbonyl)-4-(substituted phenyl)-pyridine-5-carboxylic acid, the ester having the general formula I

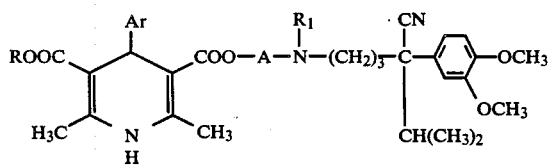

wherein
Ar represents a 3-nitrophenyl or 2,3-dichlorophenyl group,
A represents a straight chain or branched chain alkylene group having from 2 to 6 carbon atoms,
R represents a straight chain or branched chain alkyl group having from 1 to 6 carbon atoms, optionally mono-substituted by an alkoxy group having from 1 to 6 carbon atoms, and
$R_1$ represents an alkyl group having from 1 to 4 carbon atoms, or a stereoisomer or pharmaceutically acceptable acid addition salt of said ester.

* * * * *